(12) United States Patent
Taillefer et al.

(10) Patent No.: US 9,272,274 B2
(45) Date of Patent: Mar. 1, 2016

(54) CATALYTIC SYSTEM FOR CROSS-COUPLING REACTIONS

(75) Inventors: Marc Taillefer, Vailhauques (FR); Ning Xia, Montepellier (FR); Florian Monnier, Montpellier (FR); Anis Tlili, Montpellier (FR)

(73) Assignee: CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 683 days.

(21) Appl. No.: 12/746,099

(22) PCT Filed: Dec. 8, 2008

(86) PCT No.: PCT/IB2008/003715
§ 371 (c)(1),
(2), (4) Date: Jul. 12, 2010

(87) PCT Pub. No.: WO2009/071997
PCT Pub. Date: Jun. 11, 2009

(65) Prior Publication Data
US 2011/0306782 A1    Dec. 15, 2011

Related U.S. Application Data

(60) Provisional application No. 60/996,830, filed on Dec. 6, 2007.

(51) Int. Cl.
*B01J 31/26* (2006.01)
*B01J 31/30* (2006.01)
*C07B 37/04* (2006.01)
*B01J 31/22* (2006.01)
*B01J 31/18* (2006.01)

(52) U.S. Cl.
CPC .......... *B01J 31/2204* (2013.01); *B01J 31/1805* (2013.01); *B01J 31/2208* (2013.01); *B01J 31/26* (2013.01); *B01J 31/30* (2013.01); *C07B 37/04* (2013.01); *B01J 2231/4205* (2013.01); *B01J 2231/4277* (2013.01); *B01J 2231/4283* (2013.01); *B01J 2231/4288* (2013.01); *B01J 2531/16* (2013.01); *B01J 2531/842* (2013.01)

(58) Field of Classification Search
CPC ............... B01J 31/2204; B01J 31/1805; B01J 31/2208; B01J 31/26; B01J 31/30; B01J 2231/4205; B01J 2231/4277; B01J 2231/4283; B01J 2231/4288; B01J 2531/16; B01J 2531/842; C07B 37/04
See application file for complete search history.

(56) References Cited

U.S. PATENT DOCUMENTS 3,979,332 A * 9/1976 Kiovsky et al. ............... 502/3
7,235,576 B1 * 6/2007 Riedl et al. .................. 514/388

| 2003/0149272 | A1 | 8/2003 | Cristau et al. |
| 2003/0171593 | A1 | 9/2003 | Cellier et al. |
| 2003/0236413 | A1 | 12/2003 | Cellier et al. |
| 2004/0147390 | A1 | 7/2004 | Schanen et al. |
| 2005/0065350 | A1 | 3/2005 | Taillefer et al. |
| 2008/0269514 | A1 | 10/2008 | Knochel et al. |
| 2009/0240061 | A1 | 9/2009 | Spindler et al. |
| 2009/0326240 | A1 | 12/2009 | Taillefer et al. |

FOREIGN PATENT DOCUMENTS

| EP | 1724248 A1 | 11/2006 | | |
| WO | 02/085838 A1 | 10/2002 | | |
| WO | 2004/013094 A2 | 2/2004 | | |
| WO | 2005/023731 A3 | 3/2005 | | |
| WO | WO 2005037763 | * 4/2005 | ............... | 514/242 |
| WO | WO 2005100301 | * 10/2005 | ............... | 568/315 |

OTHER PUBLICATIONS

Grant & Hackh's Chemical Dictionary (5th Ed. 1987) at p. 148.*
Henri-Jean Cristau et al.; A General and Mild Ullmann-Type Synthesis of Diaryl Ethers; Organic Letters vol. 6, No. 6 913-916; 2004.
Buchwald et al.; A General and Efficient Copper Catalyst for the Amidation of Aryl Halides and the N-Arylation of Nitrogen Heterocycles; Massachusetts Institute of Technology; 2001.
Henri-Jean Cristau et al.; Highly Efficient and Mild Copper-Catalyzed N- and C- Arylations with Aryl Bromides and Iodides; Chem. Eur.; 2004.
Correa et al.; Iron-Catalyzed N-Arylation of Nitrogen Nucleophiles; Angewandte Chemie; 2007.
Bolm et al.; Iron-Catalyzed Reactions in Organic Synthesis; Chemical Reviews; 2004.
Bedford et al.; Simple Iron-Amine Catalysts for the Cross-Coupling of Aryl Grignards with Alkyl Halides Bearing B-Hydrogens; Chemical Communications; 2005.
Neumann et al.; Synthesis of Olefins Cross Coupling of Alkenyl Halides and Grignard Reagents Catalyzed by Iron Complexes; Journal of Organic Chemistry; vol. 40, No. 5; 1975.
Sherry et al.; The Promise and Challenge of Iron-Catalyzed Cross Coupling; Accounts of Chemical Research; 2008.
Ullmann et al.; Over Methoxy Chlorobenzoic Acid; Techn. Chemical Inst.; 1905.

* cited by examiner

*Primary Examiner* — Samantha Shterengarts
(74) *Attorney, Agent, or Firm* — ALG Intellectual Property, LLC

(57) ABSTRACT

The present invention concerns a process for creating a Carbon-Carbon bond (C—C) or a Carbon-Heteroatom bond (C-HE) by reacting a compound carrying a leaving group with a nucleophilic compound carrying a carbon atom or a heteroatom (HE) that can substitute for the leaving group, creating a C—C or C-HE bond, wherein the reaction takes place in the presence of an effective quantity of a. a catalytic system comprising a ligand and at least a metal-based catalyst, such a metal catalyst being chosen among iron or copper compounds proviso that only a single metal is present.

42 Claims, No Drawings

CATALYTIC SYSTEM FOR CROSS-COUPLING REACTIONS

An objective of the present invention is to provide an efficient catalytic system for cross-coupling reactions. Another objective is to provide a simple and easily available catalytic system which is efficient for a wide variety of cross-coupling reactions, said catalytic system being less expensive and less toxic than the catalytic systems known in the art. Other objectives will be apparent in the following specification.

It has now been found that these objectives are met in whole or in part with the subject of the present invention.

In a first aspect, the present invention relates to a process for creating a Carbon-Carbon bond (C—C) or a Carbon-Heteroatom bond (C-HE) by reacting a compound carrying a leaving group with a nucleophilic compound carrying a carbon atom or a heteroatom (HE) that can substitute for the leaving group, creating a C—C or C-HE bond, wherein the reaction takes place in the presence of an effective quantity of a catalytic system comprising a ligand and at least a metal-based catalyst, such a metal catalyst being chosen among iron or copper compounds proviso that only a single metal is present.

In a preferred embodiment the metal is either iron or copper.

Applicants have now found that the use of a single metal based compound as a catalytic system in association with a ligand, allows cross-coupling reactions between a compound carrying a leaving group and a nucleophilic compound, without it being necessary to use specific solvents.

The general scheme of the process according to the present invention may be illustrated as follows:

wherein:
  $Y$—$R^0$ represents a compound carrying a leaving group Y; and
  R-Q: represents a nucleophilic compound, R being the residue of said nucleophilic compound, and Q being a carbon atom or a heteroatom (HE) that can substitute for said leaving group Y.
  the ligand being chosen among the compound of formula I

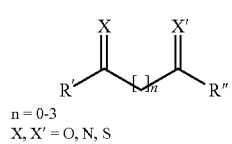

n = 0-3
X, X' = O, N, S

R' and R", which may be identical or different, represent a hydrogen atom or a C1-C20 hydrocarbon group, which may be a saturated or unsaturated acyclic linear or branched aliphatic group; a saturated, unsaturated or aromatic, monocyclic or polycyclic carbocyclic or heterocyclic group; or a concatenation of said groups; and at most one of the groups R' and R" represents hydrogen.
  the metal catalyst being chosen among iron or copper compounds as defined below. In one embodiment, the ligand is of diketone type and R' and R" may be identical or different, represent a C1-C20 hydrocarbon group linear or branched.
  More particularly R' and R" are terbutyl.

In one aspect of the process of the present invention, an arylation reaction is carried out by reacting an aromatic compound carrying a leaving group with a nucleophilic compound.

In another aspect of the process of the invention, a vinylation or alkynylation reaction is carried out by reacting a compound with a double or triple bond in the α position to a leaving group respectively. Throughout the description of the present invention, the term "arylation" is used in its broad sense since it is envisaged that the compound employed carries a leaving group which is either of the unsaturated aliphatic type, or of the carbocyclic aromatic or heterocyclic type.

The term "nucleophilic compound" means an organic hydrocarbon compound that may be acyclic or cyclic or polycyclic and comprises at least one atom carrying a free electron pair, which may or may not carry a charge, preferably a nitrogen, oxygen, sulfur, boron or phosphorus atom, or comprises a carbon atom that may donate its electron pair.

As mentioned above, the nucleophilic compound comprises at least one atom carrying a free electron pair, which can be carried by a functional group and/or a carbanion.

Examples of functional groups and/or carbanions comprising said atom that can be mentioned are:

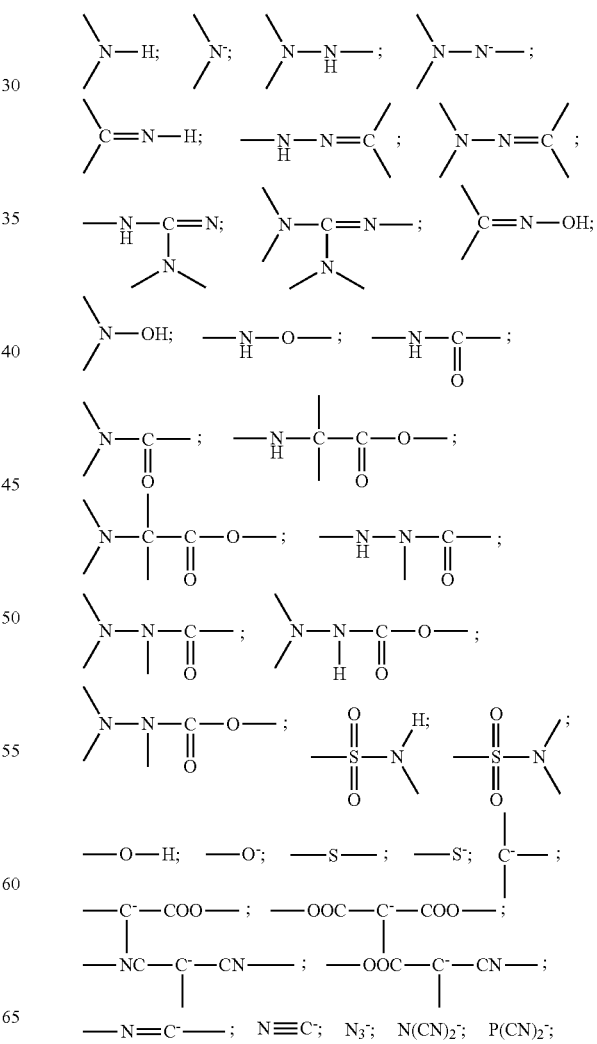

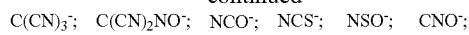
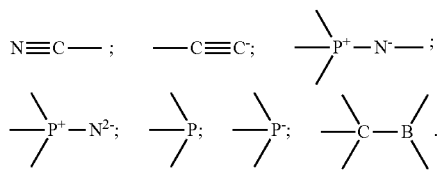

In one embodiment the nucleophilic compound is a hydroxy-containing compound.

More particularly the nucleophilic compound is a phenol, substituted or not, polysubstituted or not in any position, with linear or branched alkyl, hydroxyl or halogen.

In a further aspect of the invention, the nucleophilic compound comprises at least one nitrogen atom carrying a free electron pair included in a saturated, unsaturated, or aromatic cycle; the cycle generally containing 3 to 8 atoms.

It should be noted that when the nucleophilic compound comprises a functional group, examples of which are given above, and carries one or more negative charges, said compound is then in its salt form. The counter-ion is generally a metallic cation such as an alkali metal, preferably potassium, sodium or lithium or an alkaline-earth metal, preferably calcium, or the residue of an organometallic compound such as magnesium or zinc compound.

A first advantage of the process of the invention is the use of a single metal catalyst of either iron or copper type rather than of palladium or nickel type, i.e. a less toxic catalyst, further bringing an additional economic advantage.

A further advantage is that a wide range of cross-coupling agents, especially arylation agents, for nucleophiles can be used, not only iodides, but also bromides, chlorides or triflates, especially aryl iodides, but also aryl bromides, chlorides or triflates.

The process of the invention involves a large number of nucleophilic compounds and examples are given below by way of illustration which are not limiting in any way.

A first category of nucleophilic compounds to which the process of the invention is applicable comprises organic nitrogen-containing derivatives, more particular primary or secondary amines; hydrazine or hydrazone derivatives; amides; sulfonamides; urea derivatives or heterocyclic derivatives, preferably nitrogen-containing and/or sulfur-containing.

More precisely, the primary or secondary amines can be represented by general formula (Ia):

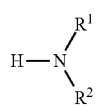

(Ia)

in which formula (Ia):
$R^1$ and $R^2$, which may be identical or different, represent a hydrogen atom or a $C_1$-$C_{20}$ hydrocarbon group, which may be a saturated or unsaturated acyclic linear or branched aliphatic group; a saturated, unsaturated or aromatic, monocyclic or polycyclic carbocyclic or heterocyclic group; or a concatenation of said groups; and at most one of the groups $R^1$ and $R^2$ represents hydrogen.

Preferred amines have formula (Ia) in which $R^1$ and $R^2$, which may be identical or different, represent a $C_1$ to $C_{15}$ alkyl group, preferably $C_1$ to $C_{10}$, a $C_3$ to $C_8$ cycloalkyl group, preferably $C_5$ or $C_6$, or a $C_6$ to $C_{12}$ aryl or arylalkyl group.

More particular examples of groups $R^1$ and $R^2$ that can be mentioned are $C_1$ to $C_4$ alkyl groups, phenyl, naphthyl or benzyl groups.

More specific examples of amines with formula (Ia) that can be mentioned are aniline, N-methyl aniline, diphenylamine, benzylamine and dibenzylamine.

The present invention does not exclude the presence of one or more insaturations in the hydrocarbon chain(s), such as one or more double and/or triple bonds, which may or may not be conjugated.

The hydrocarbon chain(s) may also be interrupted by one or more heteroatom(s) (e.g. oxygen, sulfur, nitrogen, phosphorous), and/or by a non-reactive functional group, such as for example —CO—.

It should be noted that the amino group can be in the form of anions. In such a case, the counter-ion is a metal cation, preferably an alkali metal cation, more preferably sodium or potassium. Examples of such compounds that can be cited are sodium or potassium amide.

The hydrocarbon chain can optionally carry one or more substituents (for example halogen, ester, amino or alkyl and/or arylphosphine) provided that they do not interfere.

The linear or branched, saturated or unsaturated acyclic aliphatic group can optionally carry a cyclic substituent. The term "cycle" means a saturated, unsaturated or aromatic carbocyclic or heterocyclic cycle.

The acyclic aliphatic group can be connected to the cycle via a covalent bond, a heteroatom or a functional group such as oxy, carbonyl, carboxyl, sulfonyl, and the like.

Examples of cyclic substituents that can be envisaged are cycloaliphatic, aromatic or heterocyclic substituents, in particular cycloaliphatic substituents containing 6 carbon atoms in the cycle or benzenic, said cyclic substituents themselves optionally carrying any substituent provided that they do not interfere with the reactions occurring in the process of the invention. Particular mention can be made of $C_1$ to $C_4$ alkyl or alkoxy groups.

More particular aliphatic groups carrying a cyclic substituent include cycloalkylalkyl groups, for example cyclohexylalkyl, or arylalkyl groups, preferably $C_7$ to $C_{12}$, in particular benzyl or phenylethyl.

In the above formula (Ia), groups $R^1$ and $R^2$ may also independently represent a carbocyclic group that is saturated or contains 1 or 2 unsaturated bonds in the cycle, generally $C_3$ to $C_8$, preferably with 6 carbon atoms in the cycle; said cycle can be substituted. A preferred example of this type of group that can be cited is cyclohexyl, optionally substituted with linear or branched alkyl groups containing 1 to 4 carbon atoms.

$R^1$ and $R^2$ may independently represent an aromatic hydrocarbon group, in particular a benzenic group of general formula ($F_1$):

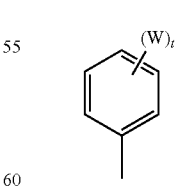

($F_1$)

in which:
t represents 0, 1, 2, 3, 4 or 5; and
W represents a group selected from linear or branched $C_1$-$C_6$ alkyl, linear or branched $C_1$-$C_6$ alkoxy, linear or branched $C_1$-$C_6$ alkylthio, —$NO_2$, —CN, halogen, $CF_3$ or a pseudohalide group.

$R^1$ and $R^2$ may also independently represent a polycyclic aromatic hydrocarbon group with cycles possibly forming between them ortho-condensed or ortho- and peri-condensed systems. A more particular example that can be cited is naphthyl; said cycle optionally being substituted.

$R^1$ and $R^2$ can also independently represent a polycyclic hydrocarbon group constituted by at least 2 saturated and/or unsaturated carbocycles or by at least 2 carbocycles, only one of which being aromatic, and forming between them ortho- or ortho- and peri-condensed systems. Generally, the cycles are $C_3$ to $C_8$, preferably $C_6$. More particular examples that can be cited are bornyl and tetrahydronaphthalene.

$R^1$ and $R^2$ can also independently represent a saturated, unsaturated or aromatic heterocyclic group, in particular containing 5 or 6 atoms in the cycle, including one or two heteroatoms such as nitrogen atoms (not substituted with a hydrogen atom), sulfur or oxygen; the carbon atoms of this heterocycle may also be substituted.

$R^1$ and $R^2$ can also represent a polycyclic heterocyclic group defined as either a group constituted by at least two aromatic or non aromatic heterocycles containing at least one heteroatom in each cycle, and forming ortho- or ortho- and peri-condensed systems between them, or a group constituted by at least one aromatic or non aromatic hydrocarbon cycle and at least one aromatic or non aromatic heterocycle forming between them ortho- or ortho- and peri-condensed systems; the carbon atoms of said cycles can optionally be substituted.

Examples of heterocyclic type groups $R^1$ and $R^2$ that can be cited include furyl, thienyl, isoxazolyl, furazanyl, isothiazolyl, pyridyl, pyridazinyl, pyrimidinyl, pyranyl, phosphino and quinolyl, naphthyridinyl, benzopyranyl or benzofuranyl groups.

The number of substituents present on each cycle depends on the carbon condensation of the cycle and on the presence or otherwise of an unsaturated bond on the cycle. The maximum number of substituents that can be carried by a cycle can readily be determined by the skilled person.

Other nucleophilic compounds encompassed by the present invention may for example be hydrazine derivatives of formulae (Ib):

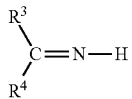

(Ib)

in which:

$R^3$ and $R^4$, which may be identical or different, have the meanings given for $R^1$ and $R^2$ in formula (Ia), and at most one of the groups $R^3$ and $R^4$ represents hydrogen.

More particularly, groups $R^3$ and $R^4$ represent a $C_1$ to $C_{15}$ alkyl group, preferably $C_1$ to $C_{10}$, a $C_3$ to $C_8$ cycloalkyl group, preferably $C_5$ or $C_6$, or a $C_6$ to $C_{12}$ aryl or aryl alkyl group. Still more particularly, $R^3$ and $R^4$ represent $C_1$ to $C_4$ alkyl, phenyl, benzyl or naphthyl.

More particularly groups $R^3$ and $R^4$ represent an aromatic group.

Other nucleophiles comprise oximes and hydroxylamines, which may be represented by general formulae (Ic) and (Id) respectively:

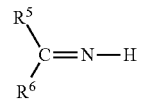

(Ic)

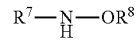

(Id)

in which formulae:

$R^5$ and $R^6$, which may be identical or different, have the meanings given for $R^1$ and $R^2$ in formula (Ia), and at most one of the groups $R^3$ and $R^4$ represents hydrogen;

$R^7$ has the meanings given for $R^1$ or $R^2$ in formula (Ia), except hydrogen; and $R^8$ represents hydrogen, a linear or branched, saturated or unsaturated acyclic aliphatic group, saturated or unsaturated, monocyclic or polycyclic, carbocyclic group; or a concatenation of said groups.

Preferred oximes or hydroxylamines are those of formulae (Ic) and (Id) respectively, wherein $R^5$, $R^6$ and $R^7$ represent $C_1$ to $C_{15}$ alkyl, preferably $C_1$ to $C_{10}$; $C_3$ to $C_8$ cycloalkyl, preferably $C_5$ or $C_6$; or $C_6$ to $C_{12}$ aryl or arylalkyl.

As more particular examples of groups $R^5$, $R^6$ and $R^7$, mention may be made of $C_1$ to $C_4$ alkyl groups, phenyl, naphthyl or benzyl. Regarding $R^8$, it preferably represents $C_1$ to $C_4$ alkyl or benzyl.

According to another aspect, the present invention involves hydrazine type nucleophilic compounds, which may be represented by the following formula (Ie):

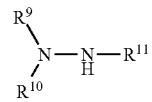

(Ie)

in which:

$R^9$, $R^{10}$ and $R^{11}$, which may be identical or different, have the meanings given for $R^1$ and $R^2$ in formula (Ia);

$R^{11}$ represents hydrogen or a protective group G; and at least one of the groups $R^9$, $R^{10}$ and $R^{11}$ does not represent hydrogen.

or $R^9$ and $R^{10}$ may together form, with the nitrogen atom carrying them, a saturated, unsaturated or aromatic, monocyclic or polycyclic $C_3$-$C_{20}$ heterocyclic group.

Preferred hydrazines are of formula (Ie) above, wherein $R^9$ and $R^{10}$, which are the same or different, represent $C_1$-$C_{15}$ alkyl, preferably $C_1$-$C_{10}$; $C_3$-$C_8$ cycloalkyl group, preferably $C_5$- or $C_6$; or $C_6$-$C_{12}$ aryl or aryl alkyl. Still preferred hydrazines are those of formula (Ie), wherein $R^9$ and $R^{10}$, which are the same or different, represent $C_1$ to $C_4$ alkyl, phenyl, benzyl or naphthyl.

$R^9$ and $R^{10}$ may be linked together, so as to form, together with the nitrogen atom carrying them, a saturated, unsaturated or aromatic, monocyclic or polycyclic $C_3$-$C_{20}$ heterocyclic group, comprising two or three ortho-condensed cycles, i.e. at least two cycles have two carbon atoms in common.

For polycyclic compounds, the number of atoms of each cycle may vary preferably between 3 and 6. According to a preferred embodiment, $R^9$ and $R^{10}$ together form cyclohexane or fluorenone.

In the above formula (Ie), $R^{11}$ preferably represents hydrogen, alkyl (preferably $C_1$-$C_{12}$), alkenyl or alkynyl (preferably $C_2$-$C_{12}$), cycloalkyl (preferably $C_3$-$C_{12}$), aryl or aryl alkyl (preferably $C_6$-$C_{12}$). Still more preferably, $R^{11}$ represents hydrogen or $C_1$-$C_4$ alkyl.

It should be noted that when the nucleophilic compound comprises a $NH_2$ group, the two hydrogen atom may react. In such a case, and in order to improve the reaction selectivity, one or the two hydrogen atoms may advantageously be blocked, using a protective agent. Such protective agents are well known in the art, and mention may be made of commonly used protective groups, such as for example acyl (acetyl, benzoyl), BOC (butyloxycarbonyl), CBZ (carbobenzoxy), FMOC (trifluoromethyloxycarbonyl) or MSOC (methanesulfenyl-2-ethoxycarbonyl). See e.g. Theodora W. Greene et al., *Protective Groups in Organic Synthesis*, 2$^{nd}$ edition, John Wiley & Sons, Inc., for the amino group protection and unprotection reactions.

Still other nucleophilic compounds that may be involved in the process of the present invention are hydrazone compounds, which may be represented by formula (If):

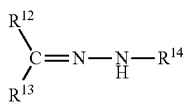

(If)

in which:

$R^{12}$, $R^{13}$ and $R^{14}$, which may be identical or different, have the meanings given for $R^1$ and $R^2$ in formula (Ia);

at most one of the groups $R^{12}$ and $R^{13}$ represents hydrogen;

or $R^{12}$ and $R^{13}$ may together form, with the carbon atom carrying them, a saturated, unsaturated or aromatic, monocyclic or polycyclic $C_3$-$C_{20}$ carbocyclic or heterocyclic group.

Preferred hydrazones are of formula (If) above, wherein $R^{12}$ and $R^{13}$, which are the same or different, represent $C_1$-$C_{15}$ alkyl, preferably $C_1$-$C_{10}$; $C_3$-$C_8$ cycloalkyl group, preferably $C_5$- or $C_6$; or $C_6$-$C_{12}$ aryl or aryl alkyl. Still preferred hydrazones are those of formula (If), wherein $R^{12}$ and $R^{13}$, which are the same or different, represent $C_1$ to $C_4$ alkyl, phenyl, benzyl or naphthyl.

$R^{12}$ and $R^{13}$ may be linked together, so as to form, together with the carbon atom carrying them, a saturated, unsaturated or aromatic, monocyclic or polycyclic $C_3$-$C_{20}$ carbocyclic or heterocyclic group, comprising two or three ortho-condensed cycles.

For polycyclic compounds, the number of atoms of each cycle may vary preferably between 3 and 6. According to a preferred embodiment, $R^{12}$ and $R^{13}$ together form cyclohexane or fluorenone.

In the above formula (If), $R^{14}$ preferably represents hydrogen, alkyl (preferably $C_1$-$C_{12}$), alkenyl or alkynyl (preferably $C_2$-$C_{12}$), cycloalkyl (preferably $C_3$-$C_{12}$), aryl or aryl alkyl (preferably $C_6$-$C_{12}$). Still more preferably, $R^{14}$ represents hydrogen or $C_1$-$C_4$ alkyl.

The invention also encompasses amide type compounds, more particularly of formula (Ig):

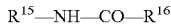

(Ig)

in which formula (Ig), $R^{15}$ and $R^{16}$ have the meanings given for $R^1$ and $R^2$ in formula (Ia).

In one embodiment $R^{15}$ is an hydrogen and $R^{16}$ is a C1-C20 hydrocarbon group linear or branched.

Examples of compounds with formula (Ig) that can be cited are oxazolidine-2-one, benzamide and acetamide.

The invention is also applicable to sulfonamide type compounds, which may be for example of formula (Ih):

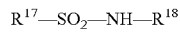

(Ih)

in which formula (Ih), $R^{17}$ and $R^{18}$ have the meanings given for $R^1$ and $R^2$ in formula (Ia).

An example of a compound with formula (Ih) comprises tosylhydrazide.

Other types of nucleophilic substrates that can be mentioned are urea derivatives such as guanidines, which can be represented by formula (Ii):

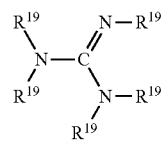

(Ii)

in which formula (Ii), groups $R_{19}$, which may be identical or different, have the meanings given for $R_1$ and $R_2$ in formula (Ia).

An example of a compound with formula (Ii) that can be cited is N,N,N',N'-tetramethylguanidine.

Still further nucleophilic compounds that may be used in the process of the present invention comprise amino-acids and derivatives thereof, e.g. of following formula (Ij):

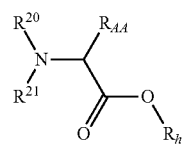

(Ij)

wherein $R_{AA}$ represents hydrogen or the residue of an amino acid, preferably hydrogen; linear or branched $C_1$-$C_{12}$ alkyl optionally carrying a functional group; $C_6$-$C_{12}$ aryl or aryl alkyl; or a functional group, preferably a hydroxyl group;

$R^{20}$ and $R^{21}$ have the meanings given for $R^1$ and $R^2$ in formula (Ia);

$R_h$ represents hydrogen; a metallic cation, preferably an alkali metal cation; or a $C_1$-$C_{12}$ hydrocarbon group, preferably $C_1$-$C_{12}$ alkyl.

In a preferred embodiment, $R_{AA}$ in formula (Ij) above represents alkyl possibly carrying a functional group, e.g. —OH, —$NH_2$, —CO—$NH_2$, —NH—CNH—, —HN—C(O)—$NH_2$, —COOH, —SH, —S—$CH_3$, or an imidazole, pyrrole, or pyrazole group.

Examples of amino-acids include glycine, cysteine, aspartic acid, glutamic acid, histidine.

Nucleophilic compounds that are well suited to use in the process of the invention are heterocyclic derivatives comprising at least one nucleophilic atom such as a nitrogen, sulfur or phosphorus atom.

More precisely, such compounds are of general formula (Ik):

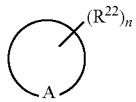

in which formula (Ik):

A represents the residue of a cycle forming all or a portion of a monocyclic or polycyclic, aromatic or non aromatic heterocyclic system, wherein one of the carbon atoms is replaced by at least one nucleophilic atom such as a nitrogen, sulfur or phosphorus atom;

$R^{22}$, which may be identical or different, represent substituents on the cycle;

n represents the number of substituents on the cycle.

The invention is applicable to monocyclic heterocyclic compounds with formula (Ik) in which A represents a saturated or unsaturated or aromatic heterocycle in particular containing 5 or 6 atoms in the cycle and possibly containing 1 or 3 heteroatoms such as nitrogen, sulfur or oxygen, at least one of which is a nucleophilic atom, such as NH or S.

A can also represent a polycyclic heterocyclic compound defined as being constituted by at least 2 aromatic or non aromatic heterocycles containing at least one heteroatom in each cycle and forming ortho- or ortho- and peri-condensed systems between them, or a group constituted by at least one aromatic or non aromatic carbocycle and at least one aromatic or non aromatic heterocycle forming ortho- or ortho- and peri-condensed systems between them.

It is also possible to start from a substrate resulting from a concatenation of a saturated, unsaturated or aromatic heterocycle as described above and of a saturated, unsaturated or aromatic carbocycle. The term "carbocycle" preferably means a cycloaliphatic or aromatic cycle containing 3 to 8 carbon atoms, preferably 6.

It should be noted that the carbon atoms of the heterocycle can optionally be substituted with groups $R^{22}$, either completely or partially.

The number of substituents present on the cycle depends on the number of atoms in the cycle and on the presence or otherwise of unsaturated bonds on the cycle. The maximum number of substituents that can be carried by the cycle can readily be determined by the skilled person.

In formula (Ik), n is preferably 0, 1, 2, 3 or 4, preferably 0 or 1.

Examples of substituents are given below, but this list is not limiting in nature.

Group or groups $R^{22}$, which may be identical or different, preferably represent one of the following groups:
  linear or branched $C_1$-$C_6$ alkyl, preferably $C_1$-$C_4$ alkyl, such as methyl, ethyl, propyl, isopropyl, butyl, isobutyl, sec-butyl or tert-butyl;
  linear or branched $C_2$-$C_6$, preferably $C_2$-$C_4$, alkenyl or alkynyl, such as vinyl or allyl;
  linear or branched $C_1$-$C_6$, preferably $C_1$-$C_4$, alkoxy or thioether, such as methoxy, ethoxy, propoxy, isopropoxy or butoxy, or alkenyloxy, preferably allyloxy or phenoxy;
  cyclohexyl, phenyl or benzyl;
  a group or function such as: hydroxyl, thiol, carboxyl, ester, amide, formyl, acyl, aroyl, amide, urea, isocyanate, thioisocyanate, nitrile, azide, nitro, sulfone, sulfonic, halogen, pseudohalogen or trifluoromethyl.

The present invention is particularly applicable to compounds of formula (Ik) in which groups $R^{22}$ more particularly represent alkyl or alkoxy.

More particularly, optionally substituted residue A represents one of the following cycles:

a monocyclic heterocycle containing one or more heteroatoms:

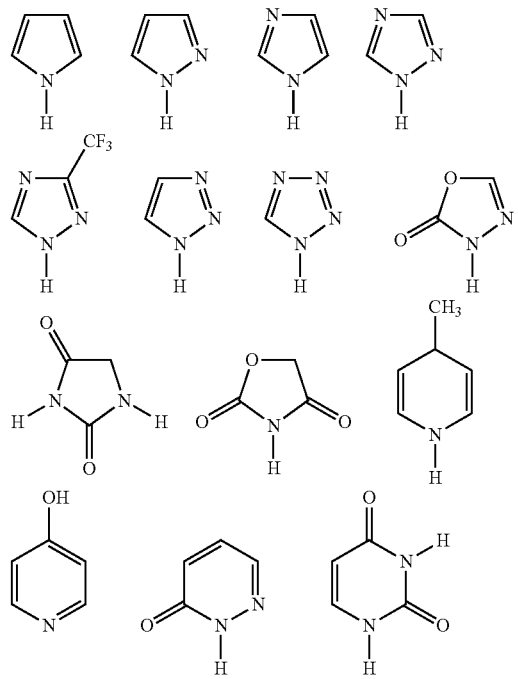

a bicycle comprising a carbocycle and a heterocycle comprising one or more heteroatoms:

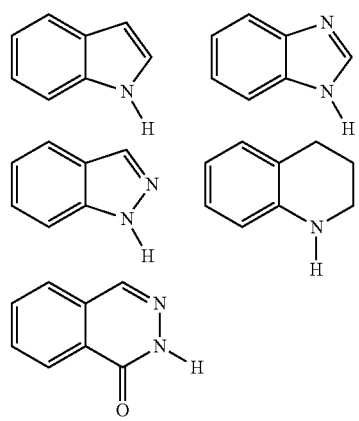

a tricycle comprising at least one carbocycle or a heterocycle comprising one or more heteroatoms:

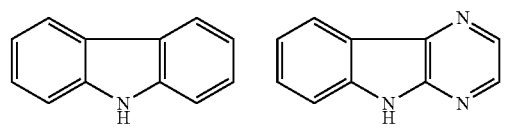

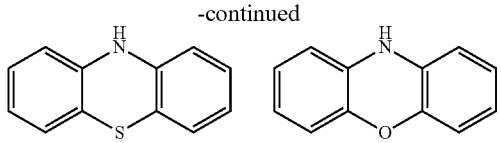

Preferred examples of heterocyclic compounds are those with formula (Ik) in which A represents a cycle such as: imidazole, pyrazole, triazole, pyrazine, oxadiazole, oxazole, tetrazole, indole, pyrrole, phthalazine, pyridazine or oxazolidine.

Among nucleophilic compounds that can also be used in the process of the invention, mention may be made of alcohol or thiol type compounds represented by the following formula (Im):

in which formula (Im):

$R^{23}$ represents a hydrocarbon group containing 1 to 20 atoms and has the meanings given for $R^1$ or $R^2$ in formula (Ia);

Z represents a $OM^1$ or $SM^1$ type group, in which $M^1$ represents a hydrogen atom or a metallic cation, preferably an alkali metal cation.

Preferred compounds have formula (Im) in which $R^{23}$ represents a hydrocarbon group containing 1 to 20 carbon atoms, which may be a linear or branched, saturated or unsaturated acyclic aliphatic group; a monocyclic or polycyclic, saturated, unsaturated or aromatic carbocyclic or heterocyclic group; or a concatenation of said groups.

More precisely, $R^{23}$ preferably represents a linear or branched saturated acyclic aliphatic group preferably containing 1 to 12 carbon atoms, more preferably 1 to 4 carbon atoms.

The invention does not exclude the presence of unsaturation on the hydrocarbon chain, such as one or more double and/or triple bonds, which may or may not be conjugated.

As for $R^1$ in formula (Ia), the hydrocarbon chain may optionally be interrupted by a heteroatom, a functional group, or may carry one or more substituents.

In formula (Im), $R^{23}$ can also represent a saturated or non saturated carbocyclic group, preferably containing 5 or 6 carbon atoms in the cycle; a saturated or non saturated heterocyclic group, containing 5 or 6 carbon atoms in the cycle including 1 or 2 heteroatoms such as nitrogen, sulfur, oxygen or phosphorus atoms; a monocyclic, aromatic heterocyclic or carbocyclic group, preferably phenyl, pyridyl, furyl, pyranyl, thiophenyl, thienyl, phospholyl, pyrazolyl, imidazolyl, pyrrolyl, or a polycyclic, aromatic heterocyclic or carbocyclic group which may or may not be condensed, preferably naphthyl.

When $R^{23}$ includes a cycle, this may also be substituted. The nature of the substituent is of no importance, provided that it does not interfere with the principal reaction. The number of substituents is generally at most 4 per cycle, usually 1 or 2. Reference should be made to the definition of $R^{22}$ in formula (Ik).

The invention also encompasses the case in which $R^{23}$ comprises a concatenation of aliphatic and/or cyclic, carbocyclic and/or heterocyclic groups.

One acyclic aliphatic group may be connected to a cycle via a covalent bond, a heteroatom or a functional group such as oxy, carbonyl, carboxy, sulfonyl, and the like.

More particular groups are cycloalkylalkyl, for example cyclohexylalkyl, or aralkyl groups containing 7 to 12 carbon atoms, in particular benzyl or phenylethyl.

The invention also encompasses a concatenation of carbocyclic and/or heterocyclic groups, more particularly a concatenation of phenyl groups separated by a covalent bond or an atom or a functional group such as: oxygen, sulfur, sulfo, sulfonyl, carbonyl, carbonyloxy, imino, carbonylimino, hydrazo or alkylene ($C_1$-$C_{10}$, preferably $C_1$)-diimino.

The linear or branched, saturated or unsaturated acyclic aliphatic group can optionally carry a cyclic substituent. The term "cycle" means a saturated, unsaturated or aromatic carbocyclic or heterocyclic cycle.

Preferred compounds with formula (Im) have general formula ($Im_1$):

in which
D represents the residue of a monocyclic or polycyclic, aromatic, carbocyclic group or a divalent group constituted by a concatenation of two or more monocyclic aromatic carbocyclic groups;

$R^{24}$ represents one or more substituents, which may be identical or different;

Z represents an $OM^1$ or $SM^1$ group in which M1 represents a hydrogen atom or a metallic cation, preferably an alkali metal cation; and n' is 0, 1, 2, 3, 4 or 5.

Examples of substituents $R^{24}$ can be found by referring to those for $R^{22}$ defined for formula (Ik).

More particular compounds with formula ($Im_1$) are those in which the residue (D) represents:

a monocyclic or polycyclic aromatic carbocyclic group with cycles that can together form an ortho-condensed system of formula ($F_{11}$):

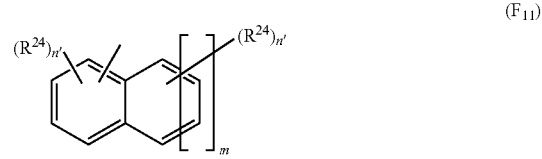

in which formula ($F_{11}$), m represents 0, 1 or 2 and symbols $R^{24}$ and n', which may be identical or different, have the meanings given above;

a group constituted by a concatenation of two or more monocyclic aromatic carbocyclic groups with formula ($F_{12}$):

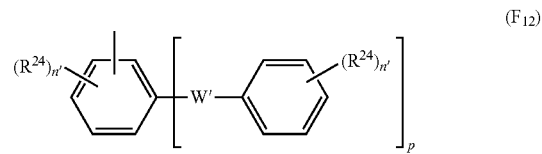

in which formula ($F_{12}$), symbols $R^{24}$ and n', which may be identical or different, have the meanings given above, p is 0, 1, 2 or 3 and W represents a covalent bond, a $C_1$-$C_4$ alkylene or alkylidene, preferably a methylene group or isopropylidene group, or a functional group such as oxy, carbonyl, carboxy, sulfonyl, and the like.

Preferred compounds with formula (Im) have formulae $(F_{11})$ and $(F_{12})$ in which:
- $R^{24}$ represents hydrogen, hydroxyl, —CHO, —NO$_2$, or a linear or branched alkyl or alkoxy group containing 1 to 6 carbon atoms, preferably 1 to 4 carbon atoms, more preferably methyl, ethyl, methoxy or ethoxy;
- W' represents a covalent bond, alkylene or alkylidene containing 1 to 4 carbon atoms or an oxygen atom;
- m is 0 or 1; n' is 0, 1 or 2; p is 0 or 1.

Illustrative examples of compounds with formula (Im) that can in particular be mentioned are:
- those in which residue D has formula $(F_{11})$ in which m and n' equal 0, such as phenol or thiophenol;
- those in which residue D has formula $(F_{11})$ in which m equals 0 and n' equals 1, such as hydroquinone, pyrocatechine, resorcin, alkylphenols, alkylthiophenols, alkoxyphenols, salicylic aldehyde, p-hydroxybenzaldehyde, methyl salicylate, p-hydroxybenzoic acid methyl ester, chlorophenols, nitrophenols or para-acetamidophenol;
- those in which residue D has formula $(F_{11})$ in which m equals 0 and n' equals 2, such as dialkylphenols, vanillin, isovanillin, 2-hydroxy-5-acetamidobenzaldehyde, 2-hydroxy-5-propionamidobenzaldehyde, 4-allyloxybenzaldehyde, dichlorophenols, methylhydroquinone or chlorohydroquinone;
- those in which residue D has formula $(F_{11})$ in which m equals 0 and n' equals 3, such as 4-bromovanillin, 4-hydroxyvanillin, trialkylphenols, 2,4,6-trinitrophenol, 2,6-dichloro-4-nitrophenol, trichlorophenols, dichloro-hydroquinones or 3,5-dimethoxy-4-benzaldehyde;
- those in which residue D has formula $(F_{11})$ in which m equals 1 and n' is 1 or more, such as dihydroxynaphthalene, 4-methoxy-1-naphthol or 6-bromo-2-naphthol;
- those in which residue D has formula $(F_{12})$ in which p is 1 and n' is 1 or more, such as 2-phenoxyphenol, 3-phenoxyphenol, phenylhydroquinone, 4,4'-dihydroxybiphenyl, isopropylidene 4,4'-diphenol (bisphenol A), bis(4-hydroxyphenyl) methane, bis(4-hydroxyphenyl)sulfone, bis(4-hydroxyphenyl)sulfoxide, tetrabromo bisphenol A.

As other nucleophilic compounds belonging to totally different families and that can be used in the process of the invention, mentioned may be made of phosphorus-containing compounds and phosphorus- and nitrogen-containing compounds, more particularly those having the following formulae:

phosphides of formula $(R^{25})_2$—P—      (In);

phosphines of formula $(R^{25})_3$—P      (Io);

phosphonium azayldiides of formula $(R^{25})_3$—P$^+$—N$^{2-}$      (Ip);

phosphonium azaylides of formula $(R^{25})_3$—P$^+$—N$^-$—R$^{26}$      (Iq);

in which formulae (In) to (Iq), the $R^{25}$ groups, that may be identical or different, and the $R^{26}$ group represent:
- $C_1$-$C_{12}$ alkyl;
- $C_5$-$C_6$ cycloalkyl;
- $C_5$-$C_6$ cycloalkyl which is substituted by one or more $C_1$-$C_4$ alkyls or $C_1$-$C_4$ alkoxys;
- phenylalkyl, the aliphatic part of which has from 1 to 6 carbon atoms;
- phenyl; or
- phenyl substituted by one or more $C_1$-$C_4$ alkyls or $C_1$-$C_4$ alkoxys, or by one or more halogen atoms.

As particularly preferred phosphorous-containing compounds, mention may be made of tricyclohexylphosphine, trimethylphosphine, triethylphosphine, tri-n-butylphosphine, tri-iso-butylphosphine, tri-tert-butylphosphine, tribenzylphosphine, dicyclohexylphenylphosphine, triphenylphosphine, dimethylphenylphosphine, diethylphenylphosphine, di-tert-butylphenylphosphine.

Other nucleophilic compounds that can be used in the process of the invention are hydrocarbon derivatives containing a nucleophilic carbon.

More particular examples are malonate type anions comprising a —OOC—HC$^-$—COO— group.

Alkyl malonate anions with formula (Ir) can be mentioned:

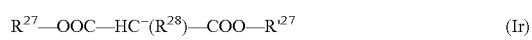

wherein:
- $R^{27}$ and $R'^{27}$, which may be identical or different, represent alkyl containing 1 to 12 atoms, preferably 1 to 4 atoms;
- $R^{28}$ is chosen from among hydrogen; $C_1$-$C_{12}$ alkyl; $C_5$-$C_6$ cycloalkyl; $C_5$-$C_6$ cycloalkyl, substituted with one or more $C_1$-$C_4$ alkyls, or $C_1$-$C_4$ alkoxys; phenyl; phenyl substituted with one or more $C_1$-$C_4$ alkyls, or $C_1$-$C_4$ alkoxys or with one or more halogen atoms; phenylalkyl, the aliphatic portion of which containing 1 to 6 carbon atoms.

It is also possible to cite malonitrile and malodinitrile type anions containing a $R^{27}$—OOC—HC$^-$($R^{28}$)—CN or NC—HC$^-$—CN group respectively, in which $R^{27}$ and $R^{28}$ have the meanings given above.

It is also possible to use nitrile type compounds containing a $R'^{28}$—CN group, wherein $R'^{28}$ has any nature and particularly has the meanings given for $R^1$ in formula (Ia) and may also represent a metallic cation, preferably an alkali cation, more preferably lithium, sodium or potassium.

Examples of nitriles that can be mentioned are acetonitrile, cyanobenzene, optionally carrying one or more substituents on the benzene ring, or ethanal cyanhydrine CH$_3$CH(OH)CN.

It is also possible to use acetylenide type compounds in the process of the invention, which may represented by the formula (Is):

in which formula $R^{29}$ is of any nature and particularly has the meanings given for $R^1$ in formula (Ia); the counter-ion is a metal cation, preferably sodium or potassium.

Particular examples that can be cited are sodium or potassium acetylide or diacetylide.

Other classes of nucleophilic compounds that can be employed in the process of the invention are profene type compounds and their derivatives represented by the following formula:

in which formula:
- $R^{30}$ has the meanings given for R1 in formula (Ia); and
- $R^{31}$ represents alkyl containing 1 to 12 atoms, preferably 1 to 4 atoms.

Preferred compounds are those with formula (It) in which $R^{30}$ represents alkyl containing 1 to 12 carbon atoms, cycloalkyl containing 5 or 6 carbon atoms and aryl containing 6 or 12 carbon atoms or a nitrogen-containing heterocycle containing 5 or 6 carbon atoms.

Nucleophilic compounds that can also be mentioned are those comprising a carbanion, the counter-ion of which is a metal and which have the following formulae:

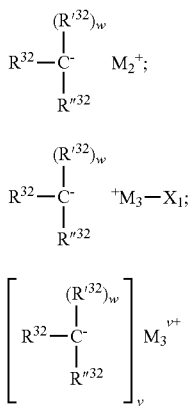

(Iu₁)

(Iu₂)

(Iu₃)

in which:

R³² represents:

alkyl containing 1 to 12 carbon atoms;

cycloalkyl containing 5 or 6 carbon atoms;

cycloalkyl containing 5 or 6 carbon atoms, substituted with one or more alkyl radicals containing 1 to 4 carbon atoms or alkoxy radicals containing 1 or 4 carbon atoms;

phenylalkyl, the aliphatic portion of which containing 1 to 6 carbon atoms;

phenyl;

phenyl substituted with one or more alkyl radicals containing 1 to 4 carbon atoms or alkoxy radicals containing 1 to 4 carbon atoms or with one or more halogen atoms; or a saturated, unsaturated or aromatic heterocyclic group, preferably comprising 5 or 6 atoms, the heteroatom being sulfur, oxygen or nitrogen;

R'³² and R''³² represent hydrogen or a group such as R³²;

two of groups R³², R'³² and R''³² may be connected together to form a carbocycle or a saturated, unsaturated or aromatic heterocycle preferably containing 5 or 6 carbon atoms;

M₂ represents a metallic element from group (IA) of the periodic table;

M₃ represents a metallic element from groups (IIA) and (IIB) of the periodic table;

X₁ represents chlorine or bromine;

v is the valency of metal M₃; and w is 0 or 1.

In the present specification, reference is made to the periodic table published in "Bulletin de la Société Chimique de France", no. 1 (1966).

Preferred compounds with formula (Iu₁) to (Iu₃) include those in which the metals are lithium, sodium, magnesium or zinc and X₁ represents chlorine.

According to an advantageous feature, R³², R'³² and R''³² represent C₁-C₄ alkyl, cyclohexyl or phenyl; or said groups may form a benzene or pyridine or thiophene cycle.

As examples, mention may be made of n-butyllithium, t-butyllithium, phenyllithium, methyl- or ethyl- or phenyl-magnesium bromide or chloride, diphenylmagnesium, dimethyl- or diethyl-zinc, cyclo-pentadienezinc, and ethyl zinc chloride or bromide.

Still other nucleophilic compounds that can be used in the process of the present invention include boronic acids or their derivatives, more particularly those with the following formula (Iv):

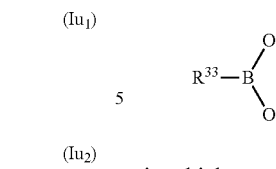

(Iv)

in which:

R³³ represents a monocyclic or polycyclic, aromatic, carbocyclic or heterocyclic group;

T¹ and T², which may be identical or different, represent hydrogen, linear or branched, saturated or unsaturated aliphatic group containing from 1 to 20 carbon atoms, or a R³³ group.

More precisely, the boronic acid or derivative has formula (Iv) in which R³³ represents an aromatic carbocyclic or heterocylic group. R³³ can have the meanings given above for D in formula (Im₁). However, R³³ more particularly represents a carbocyclic group such as a phenyl, naphthyl or heterocyclic group such as a pyrrolyl, pyridyl, pyrimidyl, pyridazinyl, pyrazinyl, 1,3-thiazolyl, 1,3,4-thiadiazolyl or thienyl.

The aromatic cycle can also be substituted. The number of substituents is generally at most 4 per cycle, but usually it is 1 or 2. Reference should be made to the definition of R²² in formula (Ik) for examples of substituents.

Preferred substituents are alkyl or alkoxy groups containing 1 to 4 carbon atoms, amino, nitro, cyano, halogen or trifluoromethyl.

T¹ and T², which may be identical or different, more particularly represent hydrogen, or a linear or branched acyclic aliphatic group containing from 1 to 20 carbon atoms which may be saturated or contain one or more unsaturated bonds (i.e. double and/or triple bond(s)) in the chain, preferably 1 to 3 unsaturated bonds, preferably simple or conjugated double bonds.

T¹ and T², preferably represent an alkyl group containing from 1 to 10 carbon atoms, preferably 1 to 4, or an alkenyl group containing from 2 to 10 carbon atoms, preferably vinyl or 1-methylvinyl.

Additionally, T¹ and T² can have the meanings given for R₂₆; in particular, any cycle can also carry a substituent as described above.

Preferably, R³³ represents a phenyl group.

The scope of the present invention encompasses derivatives of boronic acids such as anhydrides and esters, more particularly alkyl esters containing 1 to 4 carbon atoms.

Particular examples of arylboronic acids that can be cited are: benzeneboronic acid, 2-thiopheneboronic acid; 3-thiopheneboronic acid; 4-methylbenzeneboronic acid, 3-methylthiophene-2-boronic acid, 3-amino-benzeneboronic acid, 3-aminobenzeneboronic acid hemisulfate, 3-fluorobenzeneboronic acid, 4-fluorobenzeneboronic acid, 2-formylbenzeneboronic acid, 3-formylbenzeneboronic acid, 4-formylbenzeneboronic acid, 2-methoxybenzeneboronic acid, 3-methoxybenzeneboronic acid, 4-methoxybenzeneboronic acid, 4-chlorobenzeneboronic acid, 5-chlorothiophene-2-boronic acid, benzo[b]furan-2-boronic acid, 4-carboxybenzeneboronic acid, 2,4,6-trimethylbenzeneboronic acid, 3-nitrobenzeneboronic acid, 4-(methylthio)benzeneboronic acid, 1-naphthaleneboronic acid, 2-naphthaleneboronic acid, 2-methoxy-1-naphthaleneboronic acid, 3-chloro-4-fluorobenzeneboronic acid, 3-acetamidobenzeneboronic acid, 3-trifluoromethylbenzeneboronic acid, 4-trifluoromethylbenzeneboronic acid, 2,4-dichlorobenzeneboronic acid, 3,5-dichlorobenzeneboronic acid, 3,5-bis-(trifluoromethyl)benzeneboronic acid, 4,4'-biphenyldiboronic acid, and esters and anhydrides of said acids.

The present text provides lists of nucleophilic compounds that are in no way limiting and any type of nucleophilic compound can be envisaged.

As stated above and in accordance with the process of the present invention, a —C—C or —C-HE- (wherein HE is O, S, P, N, Si, B, and the like) bond can be created by reacting a nucleophilic compound, such as those described herein before, with a compound carrying a leaving group, typically a compound comprising one unsaturated bond in the position α to a leaving group.

More precisely, the compound carrying a leaving group is represented by general formula (II):

$$Y—R^0 \quad (II)$$

in which formula $R^0$ represents a hydrocarbon group containing from 2 to 20 carbon atoms and optionally has at least one unsaturation (a double or a triple bond) in the position α to a leaving group Y, or represents a monocyclic or polycyclic, aromatic, carbocyclic and/or heterocyclic group.

In accordance with the process of the invention, the compound of formula (I) is reacted with a compound of formula (II) in which:
  $R^0$ represents an aliphatic hydrocarbon group optionally containing at least one double bond and/or one triple bond in the position α to the leaving group or a cyclic hydrocarbon group containing an unsaturated bond carrying a leaving group; or
  $R^0$ represents a monocyclic or polycyclic, aromatic, carbocyclic and/or heterocyclic group;
  Y represents a leaving group, preferably halogen or a sulfonic ester group of formula —OSO$_2$—$R^e$, in which $R^e$ is a hydrocarbon group.

The compound of formula (II) will henceforth be designated as the "compound carrying a leaving group".

In the formula for the sulfonic ester group, $R^e$ is a hydrocarbon group of any nature. However, given that Y is a leaving group, it is advantageous from an economic viewpoint for $R^e$ to be simple in nature, and more particularly to represent a linear or branched alkyl group containing from 1 to 4 carbon atoms, preferably methyl or ethyl, but it can also represent phenyl or tolyl or trifluoromethyl, for example.

Preferred group Y is a triflate group, which corresponds to a group $R^e$ representing trifluoromethyl.

Bromine or chlorine atoms constitute preferred leaving groups.

More particularly, compounds of formula (II) used in accordance with the process of the present invention can be classified into three groups:
(1) aliphatic type compounds, carrying a double bond which can be represented by formula (IIa):

in which formula (IIa):
  $R^{34}$, $R^{35}$ and $R^{36}$, which may be identical or different, represent hydrogen or a hydrocarbon group containing 1 to 20 carbon atoms, which can be a linear or branched, saturated or unsaturated aliphatic group; a monocyclic or polycyclic, saturated, unsaturated or aromatic carbocyclic or heterocyclic group; or a concatenation of aliphatic and/or carbocyclic and/or heterocyclic groups as defined above;
  Y represents the leaving group, as defined above;
(2) aliphatic type compounds, carrying a triple bond which can be represented by formula (IIb):

$$R^{34}—C≡C—Y \quad (IIb)$$

in which formula (IIb):
  $R^{34}$ has the same definition as the one given for formula (IIa); and
  Y represents the leaving group, as defined above;
(3) aromatic type compounds, hereinafter designated as "haloaromatic compound" and which can be represented by formula (IIc):

in which formula (IIc):
  E represents the residue of a cycle forming all or a portion of a monocyclic or polycyclic, aromatic, carbocyclic and/or heterocyclic system;
  $R^{37}$, which may be identical or different, represents substituents on the cycle;
  Y represents a leaving group as defined above; and
  n" represents the number of substituents on the cycle.

The invention is applicable to unsaturated compounds of formula (IIa) or of formula (IIb) in which $R^{34}$ preferably represents a saturated linear or branched acyclic aliphatic group, preferably containing from 1 to 12 carbon atoms.

The invention does not exclude the presence of a further unsaturated bond on the hydrocarbon chain, such as a triple bond or one or more double bonds, which may or may not be conjugated.

The hydrocarbon chain can optionally be interrupted with a heteroatom (for example oxygen or sulfur) or by a functional group, provided that it does not react; in particular, a group such as —CO— can be cited.

The hydrocarbon chain can optionally carry one or more substituents provided that they do not react under the reaction conditions; particular mention can be made of halogen, nitrile or trifluoromethyl.

The linear or branched, saturated or unsaturated acyclic aliphatic group can optionally carry a cyclic substituent. The term "cycle" means a saturated, unsaturated or aromatic, carbocyclic or heterocyclic cycle.

The acyclic aliphatic group can be connected to the cycle via a covalent bond, a heteroatom or a functional group such as oxy, carbonyl, carboxy, sulfonyl, and the like.

Examples of cyclic substituents that may be mentioned are cycloaliphatic, aromatic or heterocyclic substituents, in particular cycloaliphatic containing 6 carbon atoms in the cycle, or benzenic substituents, said cyclic substituents themselves optionally carrying any substituent provided that these do not interfere with the reactions occurring in the process of the invention. Particular mention can be made of alkyl or alkoxy groups containing from 1 to 4 carbon atoms.

More particular examples of aliphatic groups carrying a cyclic substituent are aralkyl groups containing 7 to 12 carbon atoms, in particular benzyl or phenylethyl.

In formulae (IIa) and/or (IIb), $R^{34}$ can also represent a carbocyclic group that may or may not be saturated, preferably containing 5 or 6 carbon atoms in the cycle, preferably cyclohexyl; a heterocyclic group, which may or may not be saturated, in particular containing 5 or 6 carbon atoms in the cycle 1 or 2 of which are heteroatoms such as nitrogen, sulfur or oxygen; a monocyclic aromatic carbocyclic group, preferably phenyl, or a polycyclic aromatic carbocyclic group, which may or may not be condensed, preferably naphthyl.

Regarding $R^{35}$ and $R^{36}$, they preferably represent hydrogen or alkyl containing from 1 to 12 carbon atoms, or phenyl or aralkyl group containing from 7 to 12 carbon atoms, preferably benzyl.

In formulae (IIa) and/or (IIb), $R^{34}$, $R^{35}$ and $R^{36}$ more particularly represent hydrogen or else $R^{34}$ represents phenyl and $R^{35}$ and $R^{36}$ represent hydrogen.

It should be noted that $R^{34}$ and $R^{35}$ may also represent a functional group, provided that it does not interfere within the coupling reaction. As examples, mention may be made of functional groups such as amido, ester, ether, cyano.

Examples of compounds of formulae (IIa) and (IIb) include vinyl chloride or bromide, β-bromo- or β-chlorostyrene, or bromoalkyne or iodoalkyne.

The invention is of particular application to haloaromatic compounds of formula (IIc) in which E is the residue of a cyclic compound, preferably containing at least 4 carbon atoms in its cycle, preferably 5 or 6, optionally substituted, and representing at least one of the following cycles:
  a monocyclic or polycyclic aromatic carbocycle, i.e., a compound constituted by at least 2 aromatic carbocycles and between them forming ortho- or ortho- and peri-condensed systems, or a compound constituted by at least 2 carbocycles, only one of which is aromatic and between them forming ortho- or ortho- and peri-condensed systems;
  a monocyclic aromatic heterocycle containing at least one of heteroatoms P, O, N or S or a polycyclic aromatic heterocycle, i.e., a compound constituted by at least 2 heterocycles containing at least one heteroatom in each cycle wherein at least one of the two cycles is aromatic and between them forming ortho- or ortho- and pert-condensed systems, or a compound constituted by at least one carbocycle and at least one heterocycle at least one of the cycles being aromatic and forming between them ortho- or ortho- and pert-condensed systems.

More particularly, optionally substituted residue E preferably represents the residue of an aromatic carbocycle such as benzene, an aromatic bicycle containing two aromatic carbocycles such as naphthalene; or a partially aromatic bicycle containing two carbocycles one of which is aromatic, such as tetrahydro-1,2,3,4-naphthalene.

The invention also envisages the fact that E can represent the residue of a heterocycle provided that it is more electrophilic than compound of formula (Ik).

Particular examples that can be cited are aromatic heterocycle such as furan or pyridine; aromatic bicycle comprising an aromatic carbocycle and an aromatic heterocycle such as benzofuran or benzopyridine; partially aromatic bicycle comprising an aromatic carbocycle and a heterocycle such as methylenedioxybenzene; aromatic bicycle comprising two aromatic heterocycles such as 1,8-naphthylpyridine; partially aromatic bicycle comprising a carbocycle and an aromatic heterocycle such as 5,6,7,8-tetrahydroquinoline.

In the process of the invention, a haloaromatic compound of formula (IIc) is preferably used, in which E represents an aromatic nucleus, preferably benzene or naphthalene.

The aromatic compound of formula (IIc) can carry one or more substituents.

In the present specification, the term "one or more" generally means less than 4 substituents $R^{37}$ on the aromatic nucleus. Reference should be made to the definitions of $R^{22}$, in formula (Ik) for various examples of substituents.

$R^{37}$ may also represent a saturated, unsaturated or aromatic heterocycle comprising 5 or 6 atoms and comprising sulfur, oxygen or nitrogen as the heteroatom. Pyrazolyl or imidazolyl groups can be typically cited in this respect.

In formula (IIc), n" is 0, 1, 2, 3 or 4, preferably 1 or 2.

Examples of compounds of formula (IIc) include p-chlorotoluene, p-bromoanisole and p-bromotrifluorobenzene.

The quantity of compound carrying a leaving group of formula (II), preferably of either formula (IIa), (IIb) or (IIc), is generally expressed with respect to the quantity of nucleophilic compound and may vary in great proportions, advantageously is close to stoichiometry. The ratio between the number of moles of compound carrying a leaving group and the number of moles of nucleophilic compound is usually in the range 0.1 to 2.0, preferably in the range 0.5 and 1.5, more preferably in the range 0.8 and 1.2, for example in the range 0.9 and 1.1.

In one embodiment the compound carrying a leaving group is of formula IId:

(IId)

In which:
  $R_0''$ is an halogen,
  $R_0'$ represent a nitro, nitrile, O-aryl, halogen, alkyl, acetyl or alkoxy group In accordance with the process of the invention, the nucleophilic compound, preferably of formulae (Ia) to (Iv), is reacted with a compound carrying a leaving group, preferably of formula (II), more preferably of formula (IIa), (IIb), (IIc) or II(d) in the presence of an effective quantity of a single metal catalytic system.

Iron-based catalysts to be used in the present invention are known compounds.

As examples of iron-based catalysts useful in the present invention, mention may be made of, among others, metallic iron, oxides of iron(II) or iron(III), hydroxides of iron(II) or iron(III), organic or inorganic salts of iron(II) or iron(III) and iron(II) or iron(III) complexes with common usual ligands.

Preferred examples of iron-based catalysts include, but are not limited to, iron(0), As examples of iron-based catalysts useful in the present invention, mention may be made of, among others, iron(0), iron halides (ex: iron(II) iodide, iron (II) bromide, iron(III) bromide, iron(II) chloride, iron(III) chloride, iron(II) fluoride, iron(III) fluoride), iron oxides or hydroxides (ex: iron(II) oxide, iron(III) oxide, iron(III) hydroxide), iron nitrates (ex: iron(II) nitrate, iron(III) nitrate), iron sulfates, sulfides or sulfites (ex: iron(II) sulfate, iron(III) sulfate, iron(II) sulfite, iron sulfide, iron disulfide), iron phosphates (ex: iron(III) phosphate), iron perchlorates (ex: iron (III) perchlorate) or iron organic salts in which the counter anion involves at least one carbon atom (ex: iron(II) acetate, iron(III) acetate, iron(III) trifluoromethylsulfonate, iron(II) methylate, iron(III) methylate, iron(III) acetylacetonate).

Mixtures of two or more iron-based catalysts may also be used. Preferred iron-based catalysts are organic or inorganic salts of iron(III), more preferably iron(III) chloride, iron(III) acetate, iron(III) acetylacetonate [Fe(acac)$_3$].

Similarly, copper-based catalysts are known compounds and are effective in the process of the invention, when used in association with the above-mentioned iron-based catalyst.

Examples of copper-based catalysts, mention may be made of, among others, metallic copper, oxides of copper(I) or copper(II), hydroxides of copper(I) or copper(II), organic or inorganic salts of copper(I) or copper(II) and copper(I) or copper(II) complexes with common usual ligands.

Preferred examples of copper-based catalysts include, but are not limited to, copper(0), copper halides (ex: copper(I) iodide, copper(I) bromide, copper(II) bromide, copper(I) chloride, copper(II) chloride), copper oxides or hydroxides (ex: copper(I) oxide, copper(II) oxide, copper(II) hydroxide), copper nitrates (ex: copper(I) nitrate, copper(II) nitrate), copper sulfates or sulfites (ex: copper(I) sulfate, copper(II) sulfate, copper(I) sulfite), copper organic salts in which the counter anion involves at least one carbon atom (ex: copper (II) carbonate, copper(I) acetate, copper(II) acetate, copper (II) trifluoromethylsulfonate, copper(I) methylate, copper(II) methylate, copper(II) acetylacetonate).

Preferred copper-based catalysts are copper(0) (Cu), copper(I) iodide (CuI), copper(II) oxide (CuO), copper(II) acetylacetonate [$Cu(acac)_2$], $CuI+Cu(acac)_2$.

In one embodiment, the catalytic system is chosen from among copper (I) bromide, copper (I) iodide, iron (III) chloride or iron (II) chloride.

The amount of metal catalyst involved in the process of the present invention, expressed as the molar ratio between (number of moles of metal) and the number of moles of the nucleophilic compound, is generally in the range 0.001 to 0.5, preferably 0.01 to 0.1.

The amount of ligand involved in the process of the present invention, expressed as the molar ratio between (number of moles of ligand) and the number of moles of the nucleophilic compound, is generally in the range 0.05 to 1, preferably 0.1 to 0.5.

A base, the function of which is to trap the leaving group, is also used in the process of the invention.

Bases suitable for the process according to the invention may be characterized by their pKa greater than about 2, preferably in the range of 4 to 30.

The pKa is defined as the ionic dissociation constant of the acid/base pair when water is used as the solvent. Reference should be made, inter alia, to the "Handbook of Chemistry and Physics", $66^{th}$ edition, p. D-161 and D-162, in order to select a base with a suitable pKa.

Suitable bases that can be cited include mineral bases such as alkali metal carbonates, bicarbonates, phosphates or hydroxides, preferably of sodium, potassium, caesium or alkaline-earth metals, preferably calcium, barium or magnesium.

It is also possible to use alkali metal hydrides, preferably sodium hydride or alkali metal alcoholates, preferably of sodium or potassium, more preferably sodium methylate, ethylate or tertiobutylate.

It is also possible to use organic bases such as tertiary amines, more particularly triethylamine, tri-n-propylamine, tri-n-butylamine, methyl dibutylamine, methyl dicyclohexylamine, ethyl diisopropylamine, N,N-diethyl cyclohexylamine, pyridine, dimethylamino-4-pyridine, N-methyl piperidine, N-ethyl piperidine, N-n-butyl piperidine, 1,2-methylpiperidine, N-methyl pyrrolidine and 1,2-dimethylpyrrolidine.

Preferred bases are alkali metal carbonates.

More particularly the base is cesium carbonate.

The quantity of base employed is such that the ratio between the number of moles of base and the number of moles of nucleophilic compound carrying the leaving group is preferably in the range 0, 1 to 4.

Where the compound carrying the leaving group may appear not to be reactive enough, it may be useful to add to the reaction mixture an iodide compound, for example of formula MI, wherein M is an alkali metal or an earth-alkali metal, preferably chosen from among lithium, sodium or potassium, preferably NaI is used. The amount of iodide compound that may be used in the reaction may vary in great proportions and is generally equal to, or about the same as, half the amount of compound carrying the leaving group, expressed in moles.

The use of said iodide compound is for example useful, advantageously where the compound carrying the leaving group is an aryl bromide, in order to enable the reaction to occur and/or to enable the reaction to be run at lower temperatures and/or improve the yield of the reaction.

The process of the invention is usually carried out in the presence of an organic solvent or mixtures of organic solvents. Convenient solvents are those that do not react under the reaction conditions.

Preferably, the solvents to be used in the process of the present invention are polar organic solvents, more preferably aprotic polar organic solvents.

Solvents that may be used in the process of the present invention are, as non limiting examples, chosen from among:
  linear or cyclic carboxamides, such as N,N-dimethylacetamide (DMAC), N,N-diethylacetamide, dimethylformamide (DMF), diethylformamide or 1-methyl-2-pyrrolidinone (NMP);
  dimethylsulfoxide (DMSO);
  hexamethylphosphotriamide (HMPT);
  tetramethyurea;
  nitro compounds such as nitromethane, nitroethane, 1-nitropropane, 2-nitropropane or mixtures thereof, and nitrobenzene;
  aliphatic or aromatic nitriles such as acetonitrile, propionitrile, butanenitrile, isobutanenitrile, pentanenitrile, 2-methylglutaronitrile or adiponitrile;
  tetramethylene sulfone (sulfolane);
  organic carbonates such as dimethylcarbonate, diisopropylcarbonate or di-n-butylcarbonate;
  alkyl esters such as ethyl or isopropyl acetate;
  halogenated or non halogenated aromatic hydrocarbons such as chlorobenzene or toluene;
  ketones, such as acetone, methylethylketone, methylisobutylketone, cyclopentanone, cyclohexanone;
  nitrogen-containing heterocycles such as pyridine, picoline and quinolines.

As stated above, it is also possible to use a mixture of solvents. Preferred solvents are carboxamides, such as DMF, acetonitrile, DMSO, NMP, DMAC.

The quantity of organic solvent to be used is depending on the nature of the selected organic solvent. Said quantity is determined so that the concentration of the compound carrying a leaving group in the organic solvent is preferably in the range 5% to 40% by weight.

According to an embodiment, the nucleophilic compound and/or the compound carrying the leaving group may be used as solvent(s) of the reaction.

The formation of the C—C or C-HE bond according to the process of the invention is generally conducted at a temperature that is advantageously in the range 0° C. to 200° C., preferably in the range 20° C. to 170° C., more preferably in the range 25° C. to 140° C.

The reaction is generally carried out at atmospheric pressure, but may also be run at higher pressures of up to 10 bars, for example.

In practice, the reaction is simple to carry out.

The order of introducing the reagents in the reaction medium is not critical. Usually, the catalytic system, the nucleophilic compound, preferably of formulae (Ia) to (Iv), the base, the compound carrying a leaving group, preferably of formula (II), more preferably of formula (IIa), (IIb), (IIc) or (IId), optionally the iodide compound and the organic solvent, are charged. The reaction medium is then heated to the desired temperature.

The progress of the reaction is monitored by following the disappearance of the compound carrying a leaving group. At the end of the reaction, a product of the type R-Q-R⁰ is obtained, wherein R, Q and R⁰ are as previously described.

The obtained compound is recovered using conventional techniques, in particular by crystallization from an organic solvent.

More specific examples of organic solvents that can be used for the crystallization step are aliphatic or aromatic, halogenated or non halogenated hydrocarbons, carboxamides and nitriles. Particular mention can be made of cyclohexane, toluene, dimethylformamide and acetonitrile.

Examples of the invention will now be given. These examples are given by way of illustration and are not limiting in nature.

General Procedure with a Copper Catalyst

After standard cycles of evacuation and back-filling with dry and pure nitrogen, an oven-dried Radley tube (Carousel "reaction stations RR98030") equipped with a magnetic stirring bar is charged with CuBr (0.1 eq.), 3,5-dimethylphenol (183 mg, 1.0 mmol), $Cs_2CO_3$ (2.5 eq.) and the aryl halide (1.5 eq.), if a solid. The tube is evacuated, back-filled with nitrogen. If a liquid, the aryl reagent is added under a stream of nitrogen by syringe at room temperature, and 2,2,6,6-tetramethyl-3,5-heptanedione (0.8 eq.) is added, followed by anhydrous and degassed DMF (2.0 mL). The tube is sealed under a positive pressure of nitrogen, stirred and heated to 135° C. for 36 h. After cooling to room temperature, the mixture is diluted with dichloromethane (~20 mL) and filtered through a plug of Celite®, the filter cake being further washed with dichloromethane (~5 mL). The filtrate is washed twice with water (~10 mL×2). Gathered aqueous phases are twice extracted with dichloromethane (~10 mL). Organic layers are gathered, dried over $Na_2SO_4$, filtered and concentrated in vacuo to yield the crude product which is then purified by silica gel chromatography with an eluent of cyclohexane and dichloromethane.

Various substrates and nucleophiles have been studied; the results are presented in the following table.

| Substrates | Nucleophiles | Yields(%) |
|---|---|---|
| chloro benzene | Phenol | 81 |
| chloro benzene | 3,5-dimethyl phenol | 82 |
| chloro benzene | 4-methyl phenol | 80 |
| chloro benzene | 4-methoxy phenol | 91 |
| chloro benzene | 4-tert-butyl phenol | 87 |
| chloro benzene | 4-fluoro phenol | 40 |
| 4-chloro anisole | 3,5-dimethyl phenol | 81 |
| 4-chloro anisole | 4-methyl phenol | 53 |
| 4-chloro toluene | 3,5-dimethyl phenol | 91 |
| 4-chloro toluene | 4-methoxy phenol | 99 |
| 4-chloro nitro benzene | 3,5-dimethyl phenol | 88 |
| 4-chloro nitrile benzene | 3,5-dimethyl phenol | 90 |
| 4-chloro acetyl benzene | 3,5-dimethyl phenol | 95 |

General Procedure with a Fe Catalyst

After standard cycles of evacuation and back-filling with dry and pure nitrogen, an oven-dried Radley tube (Carousel "reaction stations RR98030") equipped with a magnetic stirring bar is charged with $FeCl_3$ (0.1 eq.), 3,5-dimethylphenol (183 mg, 1.0 mmol), $Cs_2CO_3$ (2.5 eq.) and the aryl halide (1.5 eq.), if a solid. The tube is evacuated, back-filled with nitrogen. If a liquid, the aryl reagent is added under a stream of nitrogen by syringe at room temperature, and 2,2,6,6-tetramethyl-3,5-heptanedione (0.8 eq.) is added, followed by anhydrous and degassed DMF (2.0 mL). The tube is sealed under a positive pressure of nitrogen, stirred and heated to 135° C. for 24 h. After cooling to room temperature, the mixture is diluted with dichloromethane (~20 mL) and filtered through a plug of Celite®, the filter cake being further washed with dichloromethane (~5 mL). The filtrate is washed twice with water (~10 mL×2). Gathered aqueous phases are twice extracted with dichloromethane (~10 mL). Organic layers are gathered, dried over $Na_2SO_4$, filtered and concentrated in vacuo to yield the crude product which is then purified by silica gel chromatography with an eluent of cyclohexane and dichloromethane.

Various substrates and nucleophiles have been studied; the results are presented in the following table.

| Substrates | Nucleophiles | Yields(%) |
|---|---|---|
| iodo benzene | Phenol | 85 |
| iodo benzene | 3,5-dimethyl phenol | 91 |
| iodo benzene | 4-fluoro phenol | 80 |
| 4-iodo anisole | 3,5-dimethyl phenol | 81 |
| 4-iodo toluene | 3,5-dimethyl phenol | 81 |
| 4-iodo nitro benzene | 3,5-dimethyl phenol | 91 |
| 4-iodo nitrile benzene | 3,5-dimethyl phenol | 80 |
| 4-iodo acetyl benzene | 3,5-dimethyl phenol | 89 |
| Bromobenzene | 3,5-dimethyl phenol | 18 (20 h) |

Synthesis of 1-(4-(4-tert-butylphenoxy)phenoxy)-3,5-dimethylbenzene

Following the general procedure (135° C., 24 hours), 4-tert-butylphenol (1.5 mmol) was coupled with 4-chloroiodobenzene (1.5 mmol). Then 0.1 eq. CuBr, 0.8 eq. Ligand 2,2,6,6-tetramethyl-3,5-heptanedione, 2.5 eq, $Cs_2CO_3$ and 1.5 mmol 3,5-dimethylphenol were added under N2, and reaction was sealed and heated at 140° C. for 36 hours. The crude brown oil was purified by flash chromatography on silica gel (eluent: cyclohexane) to provide 80% yield of the desired product as an oil.

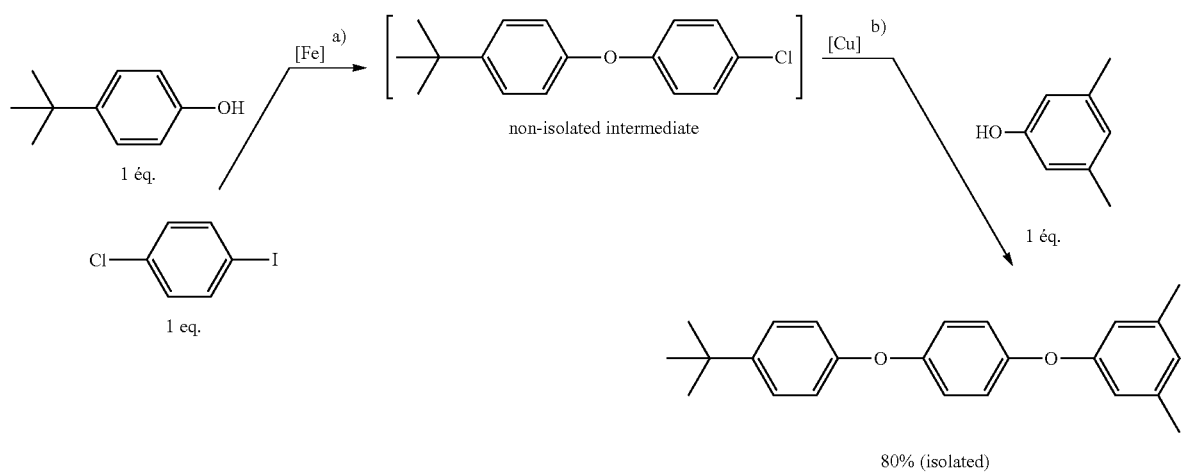

a) FeCl₃/Ligand/Cs₂CO₃/DMF
   135° C., 24 h
b) CuBr/Ligand/Cs₂CO₃/DMF
   140° C., 36 h General Procedure with a Fe Catalyst After standard cycles of evacuation and back-filling with dry and pure nitrogen, an oven-dried Radley tube (Carousel "reaction stations RR98030") equipped with a magnetic stirring bar was charged with FeCl$_2$ (12.6 mg, 0.1 mmol), cesium carbonate (651 mg, 2 mmol) then the tube was evacuated and back-filled with nitrogen. Under a stream of nitrogen at room temperature 2,2,6,6-tetramethyl-3,5-heptadione (0.125 mL, 0.6 mmol), iodobenzene (0.17 mL, 1.5 mmol), benzophenone imine (0.168 mL, 1 mmol) and followed by anhydrous and degassed DMF (2 mL).

The tube was sealed under a positive pressure of nitrogen, and stirred and heated at 140° C. for 20 hours.

After cooling to room temperature, the mixture was diluted with dichloromethane (~20 mL) and filtered through a plug of Celite. The organic layers were concentrated in vacuo to yield a brown oil. The crude product obtained was purified by silica gel chromatography with hexanes and ethyl acetate as eluent (1/1).

The corresponding coupling product was obtained in 30% yield.

Then acidic hydrolysis of the imine product was performed under classical conditions to obtain aniline in 30% yield. [1]

Another alternative to obtain the aniline compound is to deprotect the imine adduct without any purification silica gel chromatography, as followed:

After cooling to room temperature, the mixture was diluted with dichloromethane (~20 mL) and filtered through a plug of Celite. The organic layers were concentrated in vacuo to yield a brown oil.

Then acidic hydrolysis of the imine intermediate product was performed under classical conditions to obtain aniline in 30% yield. [S. L. Buchwald et al., *Tetrahedron Lett.*, 1997, 38, 6367]

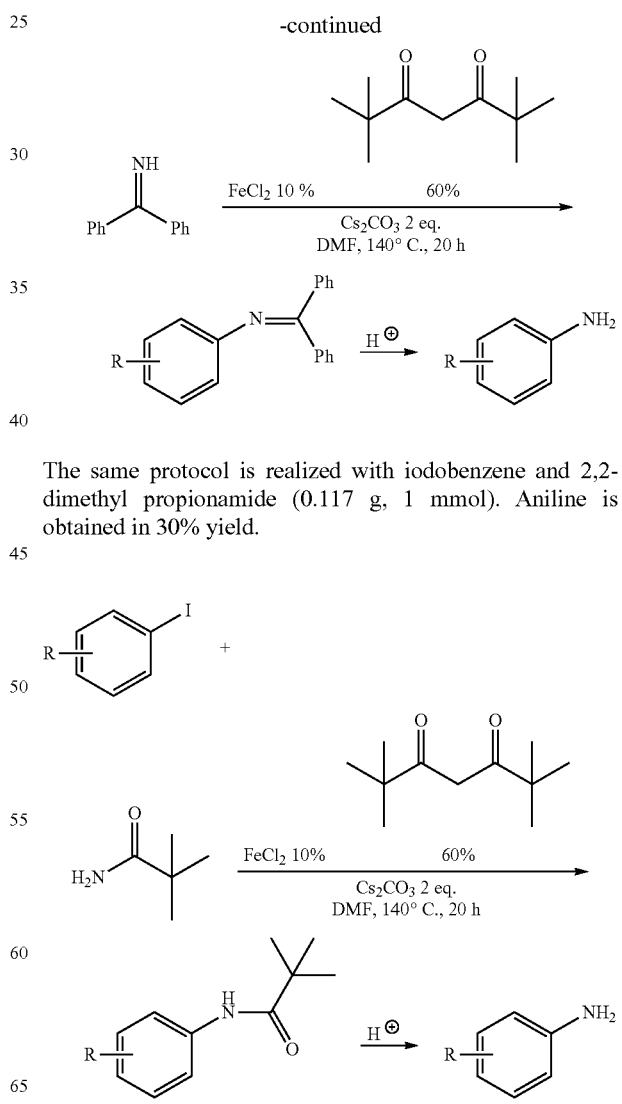

The same protocol is realized with iodobenzene and 2,2-dimethyl propionamide (0.117 g, 1 mmol). Aniline is obtained in 30% yield.

The invention claimed is:

1. A process for the preparation of a compound of the following formula:

by reaction, in the presence of an effective quantity of a catalytic system comprising at least a metal-based catalyst chosen among iron or copper, with the proviso that only a single metal is present, and a ligand of formula (I)

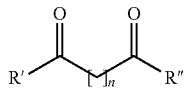

between:
a compound of formula (II)

          (II)

and a nucleophilic compound of formula (Im)

          (Im)

wherein:
$R^0$ is a hydrocarbon group containing from 2 to 20 carbon atoms and optionally having at least one unsaturation (a double or a triple bond) in the position α to Y, or is a monocyclic or polycyclic, aromatic, carbocyclic and/or heterocyclic group;

Y is a halogen;

$R^{23}$ is a $C_1$-$C_{20}$ hydrocarbon group, which may be a saturated or unsaturated acyclic linear or branched aliphatic group; a saturated, unsaturated or aromatic, monocyclic or polycyclic, carbocyclic or heterocyclic group; or a concatenation of said groups;

$M^1$ is H or a metallic cation;

R' and R", identical or different, represent a hydrogen atom or a $C_1$-$C_{20}$ hydrocarbon group, which may be saturated or unsaturated acyclic linear or branched aliphatic group; a saturated, unsaturated or aromatic, monocyclic or polycyclic, carbocyclic or heterocyclic group; or a concatenation of said groups, and at most one of the groups R' and R" represents hydrogen;

n is 0, 1, 2, or 3;

the molar ratio between the number of moles of metal of the catalyst and the number of moles of the nucleophilic compound is in the range 0.001 to 0.1.

2. The process according to claim 1, wherein the ligand is of diketone type of formula (I) and R' and R" may be identical or different, represent a C1-C20 hydrocarbon group linear or branched.

3. The process according to claim 1, wherein said compound of formula (II) is a compound with at least one unsaturation (a double or a triple bond) in the α position to Y.

4. The process according to claim 1, wherein $R^0$ in said compound of formula (II) is an aromatic group carrying a leaving group, Y.

5. The process according to claim 1 wherein the nucleophilic compound is a phenol, substituted or not, polysubstituted or not in any position, with alkyl linear or branched, hydroxyl and halogen.

6. The process according to claim 1, wherein the compound of formula (II) is represented by general formula (IIc):

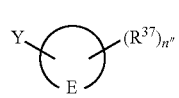          (IIc)

in which formula (IIc):
E represents the residue of a cycle forming all or a portion of a monocyclic or polycyclic, aromatic, carbocyclic and/or heterocyclic system;

$R^{37}$, which may be identical or different, represents substituents on the cycle;

Y represents a halogen as defined above; and n" is 0, 1, 2, 3 or 4.

7. The process according to claim 6, wherein the compound of formula (II) is represented by general formula (IIc), wherein E is the residue of a cyclic compound containing at least 4 carbon atoms in its cycle, optionally substituted, and representing at least one of the following cycles:

a monocyclic carbocycle or a polycyclic aromatic carbocycle constituted by at least 2 aromatic carbocycles and between them forming ortho- or ortho- and peri-condensed systems, or a compound constituted by at least 2 carbocycles, only one of which is aromatic and between them forming ortho- or ortho- and peri-condensed systems;

a monocyclic aromatic heterocycle containing at least one of heteroatoms P, O, N or S or a polycyclic aromatic heterocycle constituted by at least 2 heterocycles containing at least one heteroatom in each cycle wherein at least one of the two cycles is aromatic and between them forming ortho- or ortho- and peri-condensed systems, or a compound constituted by at least one carbocycle and at least one heterocycle at least one of the cycles being aromatic and forming between them ortho- or ortho- and peri-condensed systems.

8. The process according to claim 1, wherein the ratio between the number of moles of compound of formula (II) and the number of moles of nucleophilic compound is in the range 0.1 to 2.0.

9. The process according to claim 1, wherein the catalytic system comprises an iron-based catalyst, said iron-based catalyst being chosen from among metallic iron, oxides of iron(II) or iron(III), hydroxides of iron(II) or iron(III), organic or inorganic salts of iron(II) or iron(III) and iron(II) or iron(III) complexes with ligands.

10. The process according to claim 1, wherein said iron-based catalyst is chosen from among iron(0), iron halides, iron oxides or hydroxides, iron nitrates, iron sulfates, sulfides or sulfites, iron phosphates, iron perchlorates or iron organic salts in which the counter anion involves at least one carbon atom.

11. The process according to claim 1, wherein the catalytic system comprises a copper-based catalyst, said copper-based catalyst being chosen from among metallic copper, oxides of copper(I) or copper(II), hydroxides of copper(I) or copper(II), organic or inorganic salts of copper(I) or copper(II) and copper(I) or copper(II) complexes with ligands.

12. The process according to claim 1, wherein said copper-based catalyst is chosen from among copper(0), copper halides, copper oxides or hydroxides, copper nitrates, copper sulfates or sulfites, copper organic salts in which the counter anion involves at least one carbon atom.

13. The process according to claim 1, wherein the catalytic system is chosen from among copper(I) bromide, copper(I) iodide, iron(III) chloride, iron (II) chloride.

14. The process according to claim 1, wherein the reaction is further carried out in the presence of a base.

15. The process according to claim 14, wherein the pKa of the base is greater than about 2.

16. The process according to claim 14, wherein the base is chosen from among alkali metal carbonates, bicarbonates, phosphates or hydroxides; alkali metal hydrides; or tertiary amines.

17. The process according to claim 14, wherein the base is cesium carbonate.

18. The process according to claim 14, wherein the quantity of base employed is such that the ratio between the number of moles of base and the number of moles of aromatic compound carrying the leaving group is in the range 0.1 to 4.

19. The process according to claim 1, wherein the reaction is further carried out in the presence of a solvent.

20. The process according to claim 19, wherein the solvent is a polar organic solvent.

21. The process according to claim 19, wherein the solvent is chosen from among:
linear or cyclic carboxamides;
dimethylsulfoxide (DMSO);
hexamethylphosphotriamide (HMPT);
tetramethyurea;
nitro compounds;
aliphatic or aromatic nitriles;
tetramethylene sulfone (sulfolane);
organic carbonates;
alkyl esters;
halogenated or non halogenated aromatic hydrocarbons;
ketones; or
nitrogen-containing heterocycles.

22. The process according to claim 19, wherein the quantity of organic solvent is such that the concentration of the compound of formula (II) in the organic solvent is in the range 5% to 40% by weight.

23. The process according to claim 1, wherein the reaction is conducted at a temperature in the range 0° C. to 200° C.

24. The process according to claim 1, comprising the steps of:
charging the catalytic system, the nucleophilic compound, the base, the compound of formula (II), and the organic solvent;
heating the reaction medium to the desired temperature;
recovering the cross-coupling reaction product.

25. The process according to claim 1, wherein the reaction takes place in the presence of an effective quantity of a catalytic system comprising iron, together with 2,2,6,6-tetramethyl 3,5-heptane dione in the presence of a base.

26. The process according to claim 1, wherein the reaction takes place in the presence of an effective quantity of a catalytic system comprising copper together with 2,2,6,6-tetramethyl 3,5-heptane dione in the presence of a base.

27. The process according to claim 1, wherein the reaction is run in a carboxamide-type solvent at a temperature in the range 0° C. to 200° C.

28. The process according to claim 1, wherein the catalytic system comprises copper.

29. The process according to claim 1, wherein the catalytic system comprises iron.

30. A process for the preparation of a compound of the following formula:

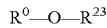

by reaction, in the presence of an effective quantity of a catalytic system comprising iron and a ligand of formula (I)

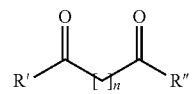

(I)

between:
a compound of formula (II)

  (II)

and a nucleophilic compound of formula (Im)

  (Im)

wherein:
$R^0$ is a hydrocarbon group containing from 2 to 20 carbon atoms and optionally having at least one unsaturation (a double or a triple bond) in the position α to Y, or is a monocyclic or polycyclic, aromatic, carbocyclic and/or heterocyclic group;
Y is a halogen;
$R^{23}$ is a $C_1$-$C_{20}$ hydrocarbon group, which may be a saturated or unsaturated acyclic linear or branched aliphatic group; a saturated, unsaturated or aromatic, monocyclic or polycyclic, carbocyclic or heterocyclic group; or a concatenation of said groups;
$M^1$ is H or a metallic cation;
n is 0, 1, 2, or 3
R' and R", identical or different, represent a hydrogen atom or a $C_1$-$C_{20}$ hydrocarbon group, which may be saturated or unsaturated acyclic linear or branched aliphatic group; a saturated, unsaturated or aromatic, monocyclic or polycyclic, carbocyclic or heterocyclic group; or a concatenation of said groups, and at most one of the groups R' and R" represents hydrogen.

31. The process according to claim 30, wherein the ligand is of diketone type of formula (I) and R' and R" may be identical or different, represent a C1-C20 hydrocarbon group linear or branched.

32. The process according to claim 30, wherein said compound of formula (II) is a compound with at least one unsaturation (a double or a triple bond) in the α position to Y.

33. The process according to claim 30, wherein $R^0$ in said compound of formula (II) is an aromatic group carrying a leaving group, Y.

34. The process according to claim 30 wherein the nucleophilic compound is a phenol, substituted or not, polysubstituted or not in any position, with alkyl linear or branched, hydroxyl and halogen.

35. The process according to claim 30, wherein the compound of formula (II) is represented by general formula (IIc):

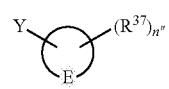

(IIc)

in which formula (IIc):
E represents the residue of a cycle forming all or a portion of a monocyclic or polycyclic, aromatic, carbocyclic and/or heterocyclic system;
$R^{37}$, which may be identical or different, represents substituents on the cycle;

Y represents a halogen as defined above; and n" is 0, 1, 2, 3 or 4.

36. The process according to claim 35, wherein the compound of formula (II) is represented by general formula (IIc), wherein E is the residue of a cyclic compound containing at least 4 carbon atoms in its cycle, optionally substituted, and representing at least one of the following cycles:
- a monocyclic carbocycle or a polycyclic aromatic carbocycle constituted by at least 2 aromatic carbocycles and between them forming ortho- or ortho- and peri-condensed systems, or a compound constituted by at least 2 carbocycles, only one of which is aromatic and between them forming ortho- or ortho- and peri-condensed systems;
- a monocyclic aromatic heterocycle containing at least one of heteroatoms P, O, N or S or a polycyclic aromatic heterocycle constituted by at least 2 heterocycles containing at least one heteroatom in each cycle wherein at least one of the two cycles is aromatic and between them forming ortho- or ortho- and peri-condensed systems, or a compound constituted by at least one carbocycle and at least one heterocycle at least one of the cycles being aromatic and forming between them ortho- or ortho- and peri-condensed systems.

37. The process according to claim 30, wherein the ratio between the number of moles of compound of formula (II) and the number of moles of nucleophilic compound is in the range 0.1 to 2.0.

38. The process according to claim 30, wherein the catalytic system comprises an iron-based catalyst, said iron-based catalyst being chosen from among metallic iron, oxides of iron(II) or iron(III), hydroxides of iron(II) or iron(III), organic or inorganic salts of iron(II) or iron(III) and iron(II) or iron(III) complexes with ligands.

39. The process according to claim 30, wherein the reaction is further carried out in the presence of a base chosen from among alkali metal carbonates, bicarbonates, phosphates or hydroxides; alkali metal hydrides; or tertiary amines.

40. The process according to claim 39, wherein the quantity of base employed is such that the ratio between the number of moles of base and the number of moles of aromatic compound carrying the leaving group is in the range 0.1 to 4.

41. The process according to claim 30, wherein the reaction is further carried out in the presence of a solvent chosen from among:
- linear or cyclic carboxamides;
- dimethylsulfoxide (DMSO);
- hexamethylphosphotriamide (HMPT);
- tetramethyurea;
- nitro compounds;
- aliphatic or aromatic nitriles;
- tetramethylene sulfone (sulfolane);
- organic carbonates;
- alkyl esters;
- halogenated or non halogenated aromatic hydrocarbons;
- ketones; or
- nitrogen-containing heterocycles.

42. The process according to claim 41, wherein the quantity of organic solvent is such that the concentration of the compound of formula (II) in the organic solvent is in the range 5% to 40% by weight.

* * * * *